US006698275B2

(12) United States Patent
Hall

(10) Patent No.: US 6,698,275 B2
(45) Date of Patent: Mar. 2, 2004

(54) ROTATIONAL RHEOMETER

(75) Inventor: Richard William Hall, Wiltshire (GB)

(73) Assignee: Bohlin Instruments Limited (GB)

( * ) Notice: Subject to any disclaimer, the term of this patent is extended or adjusted under 35 U.S.C. 154(b) by 4 days.

(21) Appl. No.: 10/175,793

(22) Filed: Jun. 21, 2002

(65) Prior Publication Data

US 2003/0233867 A1 Dec. 25, 2003

(51) Int. Cl.⁷ .............................................. G01N 11/14
(52) U.S. Cl. ...................................... 73/54.28; 73/54.43
(58) Field of Search .............................. 73/54.02, 54.28, 73/54.29, 54.31, 54.32, 54.33, 54.34, 54.43

(56) References Cited

U.S. PATENT DOCUMENTS

| | | | | |
|---|---|---|---|---|
| 4,185,493 A | * | 1/1980 | Frosch et al. | 73/54.43 |
| 4,760,734 A | * | 8/1988 | Maxwell | 73/54.34 |
| 5,587,522 A | * | 12/1996 | Selby | 73/54.28 |
| 6,240,770 B1 | * | 6/2001 | Raffer | 73/54.28 |

* cited by examiner

Primary Examiner—Michael Cygan
(74) Attorney, Agent, or Firm—Bacon & Thomas, PLLC

(57) ABSTRACT

A rotational rheometer is provided with a heat control cup located around a measuring cup having a wall thickness decreasing gradually from the bottom of the cup to its outer rim. Temperature of the heat control cup is maintained by a heat pump. The heat controlled cup has a wall thickness which is narrow at or adjacent the open end than the thickness adjacent the base of the cup.

11 Claims, 1 Drawing Sheet

ROTATIONAL RHEOMETER

BACKGROUND OF THE INVENTION

This invention relates to rotational rheometers and in particular to measuring cups for use in rotational rheometers.

Rotational rheometers (which term is intended to encompass inter alia rotary viscosimeters) are known in the prior art and typically comprise; a measuring cylinder driven to rotate by a motor via a shaft, the cylinder is received in a measuring cup which also receives a sample of material whose viscosity is to be measured. It is also known to rotate the measuring cup and sample relative to the measuring cylinder. Since temperature can affect the viscosity of many materials quite dramatically, the measuring cup, containing the sample, is usually maintained at a fixed temperature by a temperature control system.

Viscosity of a sample can be determined by measuring the torque exerted by the sample in resistance to the rotation of the measuring cylinder, parameters such as the current consumption of the motor and the phase shift of the electronic signal supplying the motor can be used to determine the torque.

Examples of rotational rheometers (more specifically rotary viscosimeters) known in the prior art are described in more detail in U.S. Pat. No. 6,240,770 B1. That patent discloses a novel combination of measuring cup and heat control system for maintaining a substantially uniform temperature distribution in the cup. The combination comprises a measuring cup surrounded by a heat control cup. An isolation gap is provided between the two cups to provide good heat isolation for the measuring cup. The two cups are in heat conducting contact in the vicinity of their upper circumferences to restrict heat conduction between them to that area. The measuring cup is constructed of a material with good heat conductivity, typically aluminium or copper. Heat is supplied to the heat control cup and is carried, by conduction, to the measuring cup where the two are in contact adjacent the rim.

SUMMARY OF THE INVENTION

It is an object of the present invention to provide an alternative means for ensuring that the temperature of a sample contained in a measuring cup of a rotational rheometer is maintained uniformly.

It is a further object of the invention to provide a rotational rheometer having a heat control system with improved effectiveness and which permits more improved accuracy in measurement of a sample's viscosity.

In accordance with the invention, a rotational rheometer is provided with a heat control cup which has a wall thickness which decreases gradually from the bottom of the cup to its outer rim. A measuring cup can be slidably received within the heat control cup and is in heat conducting communication with the heat control cup. An air gap can, optionally, be provided between the two cups, provided there is some direct heat conducting contact between them, but it is preferred there is no air gap. Temperature of the heat control cup is maintained by a heat pump, such as a Peltier block. Heat is transferred to the measuring cup through the heat conductive communication between the measuring cup and the heat control cup. The heat control cup is constructed from a material with good heat conductivity such as aluminium, copper, alloys of aluminium or copper and the like. The temperature of the sample may be monitored by means of sensors which may, for example, be located in the wall of the heat control cup and/or the sample cup.

Desirably, the walls of the heat control cup decrease in thickness continually and uniformly from the bottom of the cup to the top. The decrease in thickness may be at a monatonic level. The heat control cup is desirably surrounded by a good heat insulator. Desirably the walls of the heat control cup comprise an inner surface which extends substantially perpendicularly from the base of the cup and an outer surface which is positioned at an angle to the inner surface which is an acute angle with respect to the base of the cup. The measuring cup desirably has a wall with parallel outer and inner surfaces which are substantially perpendicular to the base of the cup. The outer surface of the measuring cup is desirably of complementary shape and size to the inner surface of the heat control cup.

DETAILED DESCRIPTION OF SPECIFIC EMBODIMENT

Figure 1:
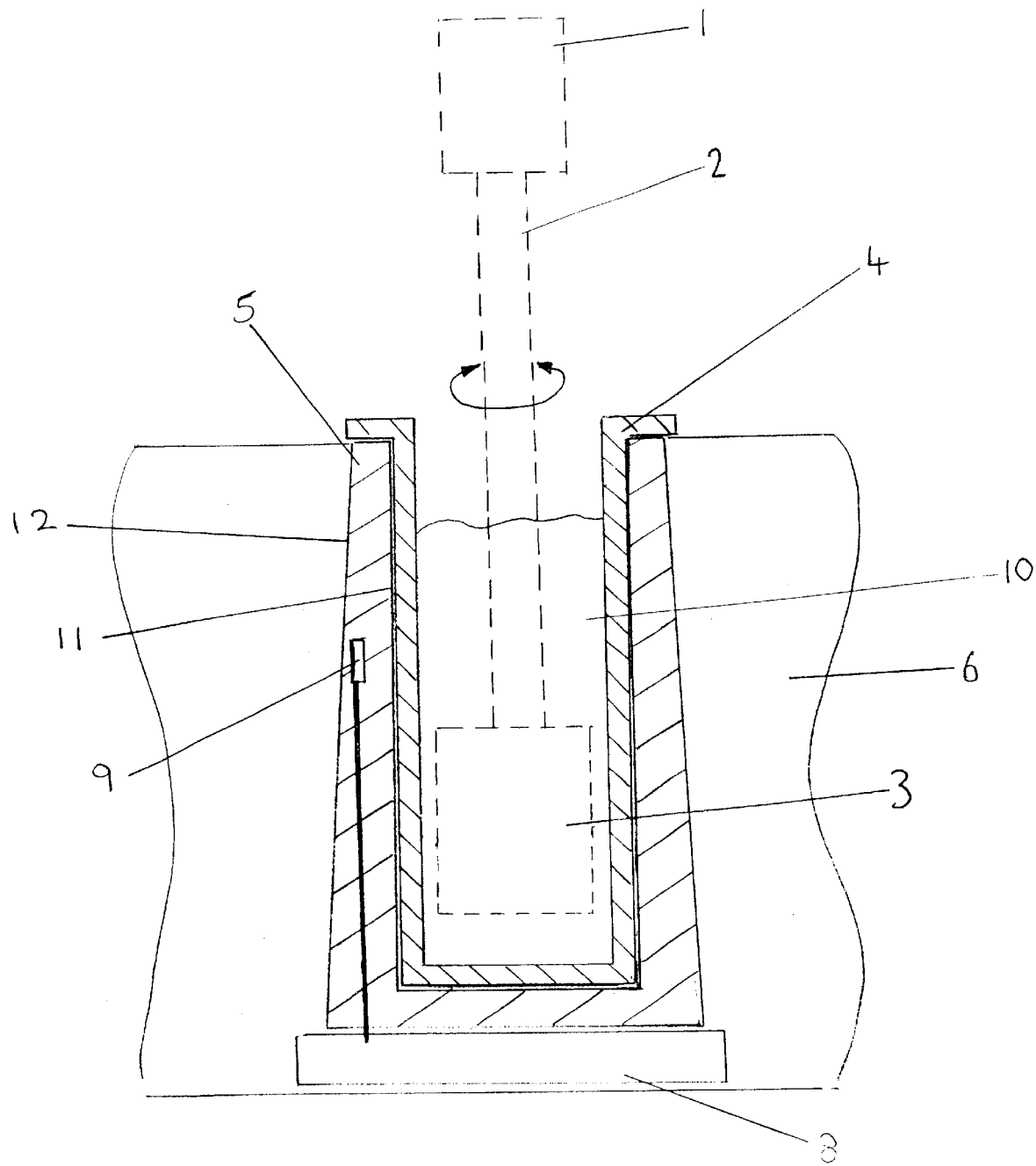
FIG. 1 illustrates schematically, a cross sectioned, side elevation view of one embodiment of a rotary viscosimeter constructed in accordance with the invention.

As can be seen from the FIGURE, the rheometer (in this case viscosimeter) comprises a motor 1 which drives a shaft 2 which in turn drives a measuring cylinder 3. These components are known in the prior art and shown in dotted outline for clarity. The measuring cylinder 3 is received in a measuring cup 4, which in turn is slidably received in a heat control cup 5. The heat control cup 5 is in turn surrounded by an insulating material 6. The rim of measuring cup 4, which has a peripheral flange sits over the rim of the heat control cup 5 thereby enclosing the heat control cup 5 in the surrounding insulation 6.

The temperature of the heat control cup 5 is maintained by a Peltier block 8 and the temperature of the heat control cup is monitored via a sensor 9 seated in a wall of the heat control cup 5. The Peltier block 8 and sensor 9 are known from the prior art. In use, test material 10 is received in the measuring cup 4 and is sheared by rotation of the measuring cylinder 3 which is placed amidst the test material 10. It is to be appreciated that in an alternative embodiment the cup may be caused to rotate whilst the cylinder remains stationary.

The heat control cup 5 has a wall with an inner surface 11 and an outer surface 12. The wall comprises solid material of high conductivity. As can be seen, the separation of the inner 11 and outer 12 surfaces decreases gradually from a position adjacent the base of the heat control cup 5 to the top of the cup. It is postulated that by reducing the quantity of heat conductive material adjacent the top rim of the cup (where there is more opportunity for heat loss relative to the bottom of the cup), the heat flux of the system is concentrated at the top of the cup thereby mitigating losses due to radiative heat loss from the top of the cup.

Since the present invention relies on the shape of the heat control cup to provide efficient heat retention, there is not a need for the isolation gap provided in U.S. Pat. No. 6,240,770 B1. The measuring cup is heated directly from all sides by direct contact with the heat control cup. It is the combination of the varying wall thickness of the heat control cup and the slidable fitting of the measuring cup therein which distinguishes the invention from prior art arrangements. This enables the components to be more compact and allows for more efficient and direct heating of the sample compared to the prior art.

What is claimed is:

1. A rotational rheometer comprising:
a measuring cylinder driven to rotate by a motor, via a shaft, the measuring cylinder being received in a measuring cup, and a heat transfer cup comprising a base and a wall extending from the base to an open end of the heat transfer cup defining a chamber in which the measuring cup is slidably received, wherein the wall of the heat transfer cup has a thickness between an outer and inner surface of the wall which is narrower at or adjacent the open end than it is at or adjacent the base, wherein the thickness of the wall decreases gradually from a position at or adjacent the base to a position at or adjacent the open end.

2. A rotational rheometer as claimed in claim 1 wherein the decrease in the thickness is monatonic.

3. A rotational rheometer as claimed in claim 1 wherein the inner surface of the wall of the heat control cup extends substantially perpendicularly from the base and the outer surface is positioned at an angle to the inner surface which is an acute angle with respect to the base of the cup.

4. A rotational rheometer as claimed in claim 1 wherein the heat control cup comprises a heat conductive material.

5. A rotational rheometer as claimed in claim 4 wherein the heat conductive material is aluminum or an alloy comprising aluminum.

6. A rotational rheometer as claimed in claim 4 wherein the heat conductive material is copper or an alloy comprising copper.

7. A rotational rheometer as claimed in claim 1 further comprising a temperature control apparatus for controlling the temperature of the heat control cup.

8. A rotational rheometer as claimed in claim 7 wherein the temperature control apparatus comprises a Peltier block and one or more temperature sensors in communication with the Peltier block.

9. A rotational rheometer as claimed in claim 8 wherein a temperature sensor is located in or on a wall of the heat control cup.

10. A rotational rheometer as claimed in claim 8 wherein a temperature sensor is located in or on a wall of the measuring cup.

11. A rotational rheometer as claimed in claim 8 wherein there are at least two temperature sensors including a first located in or on a wall of the heat control cup and a second in or on a wall of the measuring cup.

* * * * *